(12) United States Patent
Jerry, Jr. et al.

(10) Patent No.: US 8,652,211 B1
(45) Date of Patent: Feb. 18, 2014

(54) MODULAR TOE JOINT IMPLANT

(76) Inventors: Gerald J. Jerry, Jr., St. Clair, MI (US);
Louis A. Serafin, Jr., Lakeport, MI (US)

( * ) Notice: Subject to any disclaimer, the term of this patent is extended or adjusted under 35 U.S.C. 154(b) by 2086 days.

(21) Appl. No.: 11/657,383

(22) Filed: Jan. 24, 2007

Related U.S. Application Data

(60) Provisional application No. 60/762,272, filed on Jan. 26, 2006.

(51) Int. Cl.
*A61F 2/42* (2006.01)
(52) U.S. Cl.
USPC .................................................. 623/21.19
(58) Field of Classification Search
USPC .......................................... 623/21.11–21.19
See application file for complete search history.

(56) References Cited

U.S. PATENT DOCUMENTS

| | | | | |
|---|---|---|---|---|
| 4,957,510 A | * | 9/1990 | Cremascoli | 623/22.46 |
| 5,314,486 A | * | 5/1994 | Zang et al. | 623/21.19 |
| 5,326,366 A | * | 7/1994 | Pascarella et al. | 623/21.19 |
| 5,725,585 A | * | 3/1998 | Zobel | 623/21.19 |
| 6,165,925 A | * | 12/2000 | Rieger | 501/103 |
| 2004/0117025 A1 | * | 6/2004 | Reindel | 623/18.11 |
| 2004/0186580 A1 | * | 9/2004 | Steinmann | 623/20.11 |
| 2006/0074492 A1 | * | 4/2006 | Frey | 623/21.15 |

OTHER PUBLICATIONS

BioPro, Inc., Metallic Hemiarthroplasty Resurfacing Prosthesis, Surgical Technique, Brochure No. 08053.
Jerry, Jr., et al., U.S. Appl. No. 60/762,272, filed Jan. 26, 2006 A.D.
BioPro, Inc., Metallic Hemiarthroplasty Resurfacing Prosthesis, Surgical Technique, Brochure No. 08053, 1995 A.D., 2 pp.
Signal Medical Corporation, SMC Great Toe, Engineering Drawing, May 6, 2002, 1 p.

* cited by examiner

*Primary Examiner* — Thomas J Sweet
*Assistant Examiner* — Megan Wolf
(74) *Attorney, Agent, or Firm* — Christopher John Rudy

(57) ABSTRACT

Modular toe joint implant is a multi-piece device. Various sized piece(s), for example, head(s) and stem(s), can be provided in a kit or separately.

3 Claims, 2 Drawing Sheets

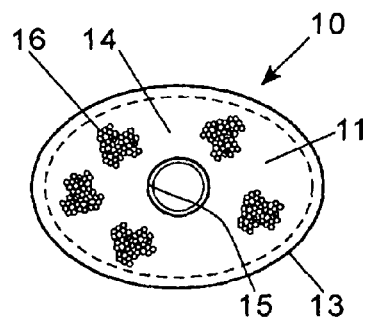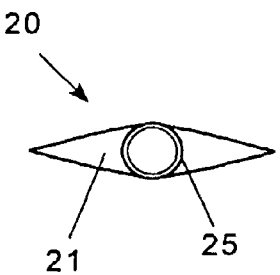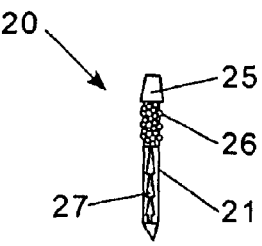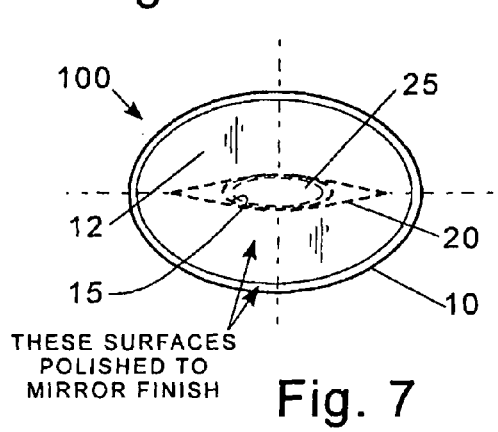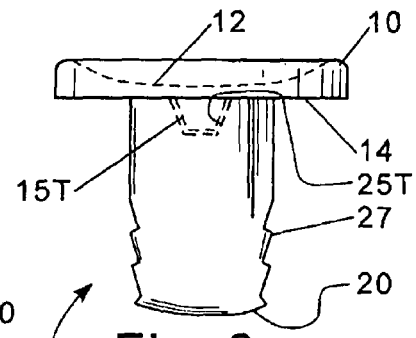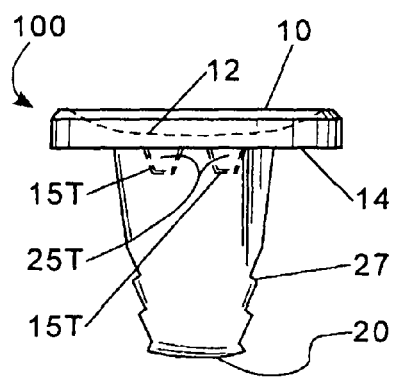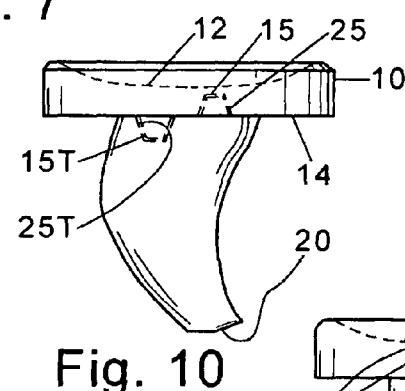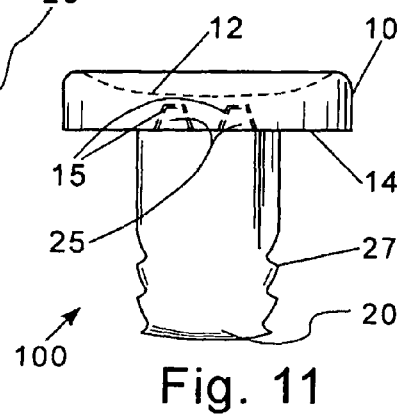

MODULAR TOE JOINT IMPLANT

This claims benefits under 35 USC 119(e) of provisional patent application No. U.S. 60/762,272 filed on Jan. 26, 2006 A.D. The specification of that application is incorporated herein by reference in its entirety.

FIELD AND PURVIEW OF THE INVENTION

This invention concerns a modular toe joint implant, piece (s) thereof or kit therewith. In particular, the implant, its piece(s) or the kit can be beneficially for the great toe.

BACKGROUND TO THE INVENTION

Decades ago, a great toe joint implant was developed by the late Charles O. Townley, M. D. As excellent as that one-piece implant is, it is not without its drawbacks. Among these include the relatively large inventory of implants required to be kept on hand to accommodate a particular patient, and a lack of options for the surgeon should bone stock of the patient require more extensive resection or should he make a mistake in surgery by resecting a little too much bone, the result of which in both of the latter cases can be a shorter than desired toe after surgery.

It is desirable to ameliorate if not overcome such drawbacks.

A FULL DISCLOSURE OF THE INVENTION

In general, the present invention provides a modular toe joint implant. Various sized piece(s), for example, head(s) and stem(s), can be provided in a kit or separately.

The invention is useful as an implant prosthesis, or piece(s) thereof, for the toe, especially for the human great toe.

Significantly, by the invention, the art is advanced in kind. By providing various sized stems and heads in a modular system, in particular, a smaller inventory may need to be kept on hand to accommodate patients, and in cases where more extensive resection is carried out by will or accident, toe length may be restored as desired. Numerous further advantages attend the invention.

The drawings form part of the specification hereof. With respect to the drawings, which are not necessarily drawn to scale, the following is briefly noted:

FIG. 4 is a rear plan view of the head of FIG. 1.

FIG. 5 is a front view of the stem of the implant of FIG. 1.

FIG. 6 is a side view of the stem of FIG. 5.

FIG. 7 is a front plan view of an alternate implant embodiment of the present invention.

FIGS. 8-11 are top plan views of other alternate implant embodiments of the present invention.

The invention can be further understood by the detail set out below, which may be read in view of the drawings. Such is to be taken in an illustrative and not necessarily limiting sense.

The present toe joint implant is a multi-piece device, beneficially of two pieces, a head and stem, which can be fixed together. Modularity is provided, for instance, by the various sized stems and heads, one of each of which may be selected as needs be in mix and match fashion, and then assembled together.

Securement of a stem to a head can be accomplished by any suitable ways or means. For instance, it may be accomplished by providing one of the head or stem, for example, with a trunnion and the complimentary piece, i.e., stem or head, respectively, with a corresponding trunnion-receiving cup. A trunnion and a cup may be provided for a head, and a stem may have a cup and a trunnion to compliment the head; or a head may have two trunnions with the cup having two cups, and so forth. Advantageously, the trunnion and cup is provided with a fixing taper such as a Morse taper, a Browne & Sharpe taper and so forth. Alternatively or in addition, a male and female threaded arrangement, a cemented connection with or without the aid of a peg and hole arrangement, and so forth may be employed. Each trunnion or peg and cup pair may generally have symmetry about a central axis such as, for instance, in a C-infinity point group as found, say, in a cylinder or conic section; in another C-n point group, say, with "n" equal to three, four, six as in an equilateral triangle prism, a square rod or a regular hexagonal rod, or an equilateral triangularly-based, a square-based, or a regular hexagon-based pyramid or truncated pyramid; a C-2 point group such as in an elliptical, ovoid, rectangular, flattened hexagonal rod or conic section; and so forth. Otherwise, it may not have such symmetry.

Any suitable material(s) can be employed to make the present implant. Thus, metals can include stainless steel, cobalt-chrome to include cobalt-chrome-molybdenum, and 6-4-1 titanium alloys. Ceramics can include alumina and zirconia, to include magnesium oxide stabilized, transformationally toughened zirconia. Other materials may include carbon fiber, polyurethane, ultra high molecular weight polyethylene, and so forth. The metals and ceramics are preferred as primary if not exclusive components. A roughened surface or porous coating may be provided for ingrowth of bone or fibrous tissue, for example, on a bone interfacing (rear) side of the head and on the stem. For instance, the porous coating may be provided by tantalum vapor deposition or sintering CoCrMo beads. Any suitable method or process can be employed as those skilled in the art understand or practice.

With reference to the drawings, great toe joint implant 100 is of two pieces: head 10 and stem 20. The implant 100 may be employed in total joint reconstruction but typically is employed in joint hemiarthroplasty.

Figure 1:
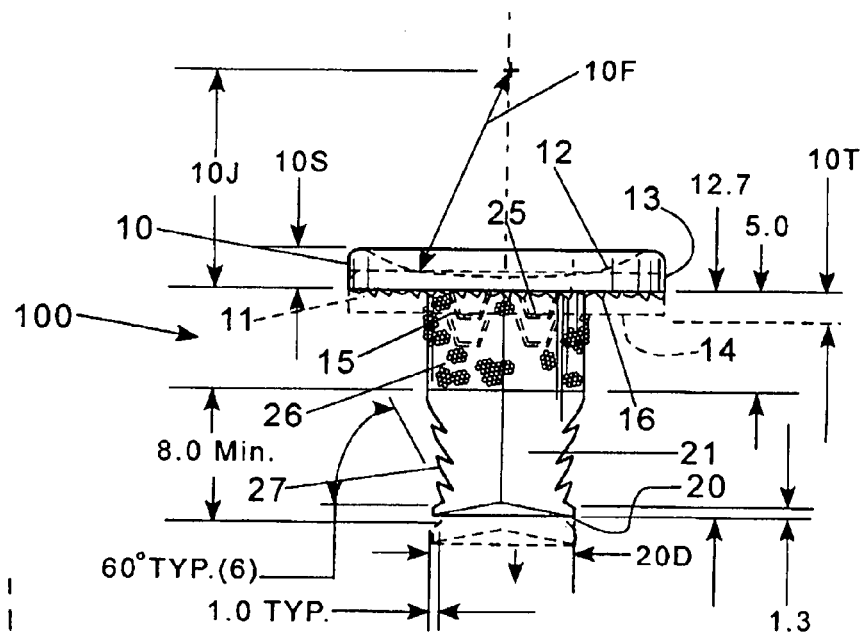
FIG. 1 is a plan view of a modular toe joint implant embodiment of the present invention, taken as a top view.
Figure 2:
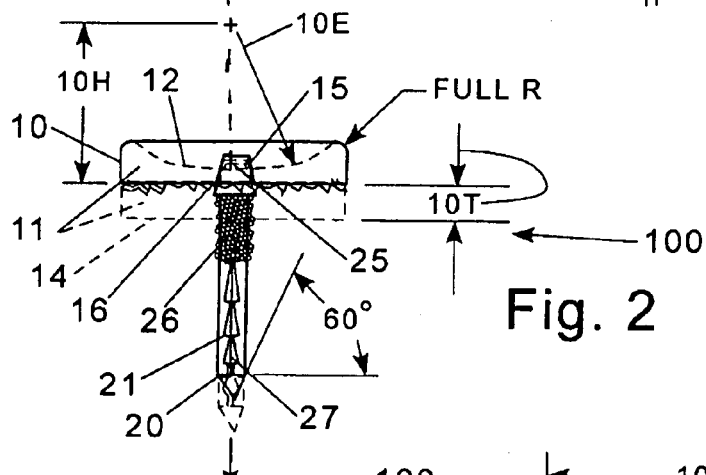
FIG. 2 is a side plan view of the implant of FIG. 1.
Figure 3:
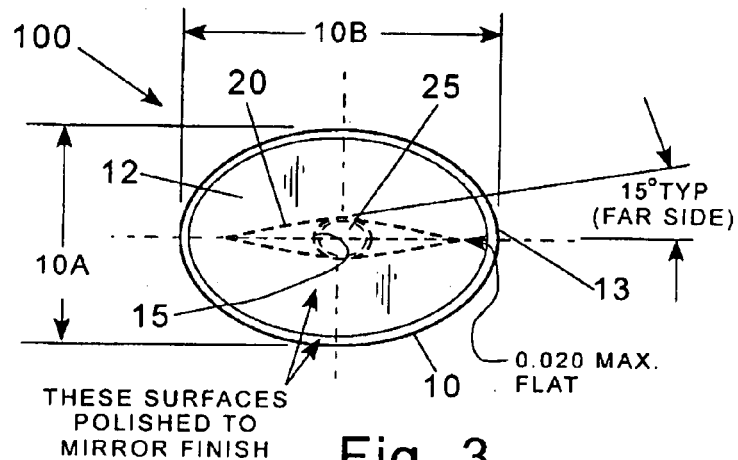
FIG. 3 is a front plan view of the implant of FIG. 1.

The head 10 includes body 11 with articular surface 12 on a front of the body; side 13; and bone-interfacing surface 14 on a rear of the body. In the rear is trunnion-receiving cup 15 (FIGS. 1-7), which is blind and may have C-infinity symmetry with a regular Morse taper to a truncated right cone (FIG. 1-6) or C-2 symmetry in a truncated elliptical cone with tapered walls in a Morse type taper (FIG. 7). As an alternative, in the rear is trunnion 15T (FIG. 8). As other alternatives, multiple cups 15 or trunnions 15T, or a combination of cup 15 and trunnion 15T may be provided (FIGS. 9-11). Rough or pore-coat bone-ingrowth engendering surface 16 may be provided, say, on the rear. The head 10 may be provided through differing dimensions 10A, 10B, 10E, 10F, 10H, 10J as first foundation or basic parts K, L, M, N, for example, in millimeters (mm) as tabulated below (Table 1).

TABLE 1

| No. | Basic K | Basic L | Basic M | Basic N |
|-----|---------|---------|---------|---------|
| 10A | 13.0 mm | 15.5 mm | 17.5 mm | 17.5 mm |
| 10B | 17.0 mm | 20.0 mm | 21.5 mm | 23.0 mm |
| 10E | 10.3 mm | 13.6 mm | 16.0 mm | 16.0 mm |
| 10F | 18.4 mm | 23.4 mm | 24.8 mm | 28.6 mm |

TABLE 1-continued

| No. | Basic K | Basic L | Basic M | Basic N |
|---|---|---|---|---|
| 10H | 11.9 mm | 15.2 mm | 17.6 mm | 17.6 mm |
| 10J | 20.0 mm | 25.0 mm | 26.4 mm | 30.2 mm |

Thus, the sides 13 in these basic parts generally have standard dimensions 10S based on such differing dimensions as noted above. Further depth or thickness 10T can be provided the head 10 to accommodate more patients where more extensive resection is carried out than provided for from the basic parts K, L, M, N. For example, the dimension 10T can extend to 5.0 mm or even 7.5 mm or more beyond the standard dimensions 10S, say, independently at each occurrence in 0.5-mm or preferably 1.0-mm increments. Heads 10 with such additional thickness 10T are beneficially, preferably provided. A plurality of heads 10 from which to select may be provided for inventory, for instance, from four to twenty-five different sized heads, say, sixteen: with four having dimensions 10T of 1.0 mm added to each of the basic K, L, M, N heads; four having dimensions 10T of 2.0 mm added to each of the basic heads K, L, M, N; four having dimensions 10T of 3.0 mm added to each of the basic heads K, L, M, N; and four having dimensions 10T of 4.0 mm added to each of the basic heads K, L, M, N.

The stem 20 includes body 21 and trunnion 25 (FIGS. 1-7) that may have C-infinity symmetry with a regular Morse taper to a truncated right cone (FIG. 1-6) or C-2 symmetry in a truncated elliptical cone with tapered walls in a Morse type taper (FIG. 7) or may have trunnion-receiving cup 25T (FIG. 8). Multiple trunnions 25, cups 25T, or a combination of trunnion 25 and cup 25T may be provided (FIGS. 9-11). The trunnion 25 of the stem 20 is received and fixed in the complimentary cup 15 of the head 10 (FIGS. 1-7), or the trunnion-receiving cup 25T of the stem 20 receives and fixes the complimentary trunnion 15T of the head 10 (FIG. 8). Rough or pore-coat bone-ingrowth engendering surface 26 and/or serrations 27 for more sure securement to the bone may also be provided. The stem 20 may be provided through differing dimensions 20D, say, in the first foundation or basic parts K, L, M, N, for example, as tabulated below (Table 2).

TABLE 2

| No. | Basic K | Basic L | Basic M | Basic N |
|---|---|---|---|---|
| 20D | 5.5 mm | 6.5 mm | 7.5 mm | 7.5 mm |

Further width (or other dimension(s)) can be provided the stem 20 to accommodate more patients than provided for from the basic parts K, L, M, N. For example, the dimension 20D can extend to a 10-mm or more dimension, say, independently at each occurrence in 0.2-mm or 0.5-mm increments. A plurality of stems 20 from which to select may be made and kept in inventory, for instance, about from two to ten different sized stems, say, four.

Desirably, the cup 15, 25T and trunnion 25, 15T have the same sized complimentary pair throughout each inventory set.

A modular great toe joint implant 100 (FIGS. 1-6) can be made of a CoCrMo alloy per ASTM F-75. Also note the following with respect thereto:
1. Surfaces to be porous coated are provided with a −45/+60 sintered bead coating per ASTM F-75—CoCrMo alloy beads, three layers.
2. HIP and heat treat after porous coating at 2165-degrees F., and 25-ksi.
3. Passivate per ASTM F-86.
4. Blast the surfaces to be porous coated with glass beads prior to providing the coating.

Note also that, unless otherwise specified, dimensions in the drawings are given in mm. Precision can be as follows:
1-place dimensions±0.3 mm.
2-place dimensions±0.1 mm.
3-place dimensions±0.01 mm.
Angular dimensions±1-degree.

Also, the dimensions 10H, 10J, 10S and 10T represent those which can be found before application of the porous coating 16.

Also, for thinner headed implants, modularity may be foregone in favor of a one-piece toe implant device. These one-piece toe implant devices may be provided with a kit that otherwise has the modular implant component(s) 10, 20 for making the implant 100 so as to provide even greater flexibility for the surgeon.

The implant 100 can be assembled after selecting the head 10 and stem 20 before or during surgery and implanted with resection of a select amount of bone at the discretion and according to the talent of the surgeon. Surgical cement may be employed.

Numerical values recited herein may be considered to be approximate or precise. In the appended claims, any approximate values are so indicated, for example, by the word, "about."

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

We claim:
1. A two-piece modular toe joint implant consisting essentially of two and only two attachable pieces to make up the implant when said two attachable pieces are assembled, wherein:
the implant is useful in joint hemiarthroplasty for a human great toe;
said two attachable pieces are a first piece of one-piece head and a second piece of a one-piece stem, which can be assembled to form the implant;
the head includes a body having a front, a side, and a rear, with a concave articular surface on the front of the body of the head and a bone-interfacing surface on the rear of the body of the head; and, in the rear of the body of the head, at least one stem-fixing feature;
the stem includes a body and at least one head-fixing feature;
the at least one stem-fixing feature of the head includes one and only one trunnion-receiving cup; and the head-fixing feature of the stem includes one and only one trunnion that can be received into the trunnion-receiving cup of the head;
the trunnion-receiving cup of the head is blind, and has a size and a taper; and the trunnion of the stem has a size and a taper corresponding to the size and taper of the trunnion-receiving cup of the head; and the trunnion-receiving cup of the head forms a truncated right cone, with the trunnion of the stem corresponding thereto.

2. The implant of claim 1, wherein the taper is a Morse taper.

3. A two-piece modular toe joint implant consisting essentially of two and only two attachable pieces to make up the implant when said two attachable pieces are assembled, wherein:

the implant is useful in joint hemiarthroplasty human great toe;

said two attachable pieces are a first piece of a one-piece head and second piece of a one-piece stem, which can be assembled to from the implant;

the head includes a body having a front, a side, and a rear, with a concave articular surface on the front of the body of the head and a bone-interfacing surface on the rear of the body of the head; and, in the rear of the body of the head, at least one stem-fixing feature;

the stem includes a body and at least one head-fixing feature; and the implant includes a porous coating for ingrowth of bone.

\* \* \* \* \*